United States Patent [19]

Reichenbach et al.

[11] Patent Number: 5,023,184

[45] Date of Patent: Jun. 11, 1991

[54] ANTIBIOTICS FROM MYXOCOCCUS

[75] Inventors: Hans Reichenbach, Wolfenbüttel; Klaus Gerth, Braunschweig; Herbert Irschik, Wolfenbüttel; Brigitte Kunze; Gerhard Höfle, both of Braunschweig; Hermann Augustiniak, Wolfenbüttel; Norbert Bedorf, Königslutter; Rolf Jansen; Wolfram Trowitzsch-Kienast, both of Braunschweig; Heinrich Steinmetz, Hildesheim-Sorsum, all of Fed. Rep. of Germany

[73] Assignees: Ciba-Geigy Corporation, Ardsley, N.Y.; Gesellschaft fur Biotechnologische Forschung mbH, Braunschweig, Fed. Rep. of Germany

[21] Appl. No.: 85,438

[22] Filed: Aug. 13, 1987

[30] Foreign Application Priority Data

Aug. 15, 1986 [CH] Switzerland .................. 3294/86

[51] Int. Cl.⁵ .................. D12N 1/20; C12P 17/18
[52] U.S. Cl. .................. 435/252.1; 435/119
[58] Field of Search .................. 435/252.1, 822, 119

[56] References Cited

U.S. PATENT DOCUMENTS 3,973,005  8/1976  Rosenberg .................. 435/170
4,248,863  2/1981  Arai .................. 424/121
4,372,947  2/1983  Arai et al. .................. 424/121

FOREIGN PATENT DOCUMENTS 173649  3/1986  European Pat. Off. .
85/01049  4/1985  World Int. Prop. O. .

OTHER PUBLICATIONS

Bergey's Manual of Determinative Bacteriology, 8th Ed., Bachanan et al., ed., 1974, Williams and Wilkins, pp. 80–81.
Onishi et al., *J. of Antibiotics*, vol. 37, 1984, pp. 13–19.
Steinmetz et al., *Eur. Cong. Biotechnol.*, 1984, pp. 643–647.
Jansen et al., *Leibigs Ann. Chem.*, 1983, vol. 7, pp. 1081–1095.
Reichenbach et al., *Pigments of Myxobacteria*, in Rosenberg (ed.), *Myxobacteria, Development and Cell Interactions*, pp. 127–137 (Springer Verlag, N.Y., (1984).
Ikeda et al., *Journal of Antibiotics*, vol. 36, pp. 1284–1289 (1983).
Frincke et al., *J. Am. Chem. Soc.*, vol. 104, No. 1, pp. 265–269 (1982).
*Tetrahedron Letters*, No. 25, pp. 2355–2358 (1979).
*Acta Cryst.*, vol. C40, pp. 1578–1580 (1984).

*Primary Examiner*—Douglas W. Robinson
*Assistant Examiner*—Irene Marx
*Attorney, Agent, or Firm*—Steven R. Lazar

[57] ABSTRACT

The invention relates to novel polycyclic alkaloids of formula

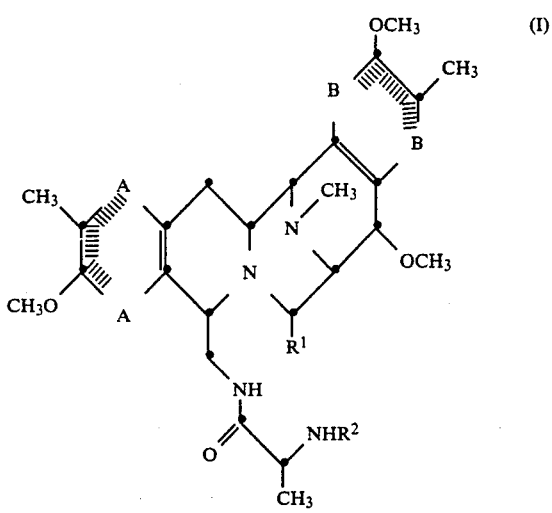

in which $R^1$ represents hydrogen or hydroxy, $R^2$ represents hydrogen or acyl and A and B, independently of one another, each represents C=O or C—OH, and wherein the dashed line represents a C=C double bond at the position of the middle bond when A or B represents C=O, or at the position of the two outer bonds when A or B represents C—OH, a process for the manufacture of these compounds by fermentation of a novel microorganism of the species *Myxococcus xanthus*, the novel microorganism itself, pharmacetical preparations that contain the novel compounds, and the use of the novel compounds as antibiotics and as tumour-inhibiting agents and for the manufacture of pharmaceutical preparations.

1 Claim, No Drawings

ANTIBIOTICS FROM MYXOCOCCUS

The invention relates to novel polycyclic alkaloids having antibiotic properties, a process for the manufacture of these compounds by fermentation of a novel microorganism of the species *Myxococcus xanthus*, the novel microorganism itself, pharmaceutical preparations containing the novel compounds, and the use of the novel compounds as antibiotics and as tumour-inhibiting agents and for the manufacture of pharmaceutical preparations.

The invention relates especially to compounds of the formula

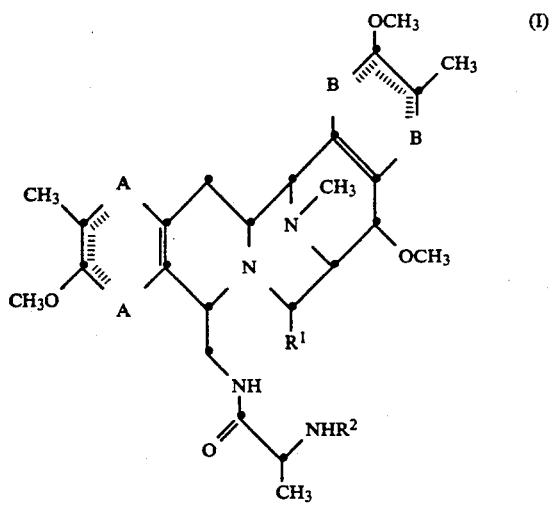

in which $R^1$ represents hydrogen or hydroxy, $R^2$ represents hydrogen or acyl and A and B, independently of one another, each represents C=O or C—OH, and wherein the dashed line represents a C=C double bond at the position of the middle bond when A or B represents C=O, or at the position of the two outer bonds when A or B represents C—OH, and salts of such compounds, especially pharmaceutically acceptable salts.

The compounds of formula I according to the invention are closely related to the compounds isolated from *Streptomyces lavendulae*, which are called saframycins. In U.S. Pat. No. 4,248,863, for example the fermentative preparation of the saframycins A, B, C, D and E is described and in U.S. Pat. No. 4,372,947 the preparation of saframycin S is described. The structure of the known saframycins is specified by T. Arai, Antimicrobial Agents and Chemotherapy 28, 5 (1985). According to this, the compounds of the formula I according to the invention differ from the known saframycins at least by the alanyl radical in the side chain, in place of which in the known saframycins there stands the acyl radical of pyruvic acid or another acyl radical, and also differ, in addition, by the meaning of the radical $R^1$ and by the methoxy group at the bridged bicyclic nucleus. Saframycin derivatives with an alanyl radical in the side chain are described in European Patent Application No. EP 173 649, but differ from the compounds according to the invention in the meaning of the radical $R^1$ and by a missing methoxy group.

The antibiotics Y-16482 α and β which are obtained by fermentation of a strain of *Pseudomonas fluorescens*, are described in European Patent Application No. EP 55 299. According to Y. Ikeda et al., J. Antibiotics 36, 1284 (1983) these compounds, also called safracins, are closely related to saframycins and thus also to the compounds of formula I according to the invention. However, the safracins differ from the novel compounds in their meaning of B (one of the groups B is C—H) and by the fact that there is no methoxy group at the bridged bicyclic nucleus.

Other closely related compounds can be isolated from the fungus Reniera sp. These compounds, called renieramycins by J. M. Frinke and D. J. Faulkner, J. Am. Chem. Soc. 104, 265 (1982) differ from the compounds of formula I according to the invention at least by the side chain which, instead of alanylaminomethyl, is (Z)-2-methyl-2-butenoyloxymethyl (an angelic acid ester) in the renieramycins.

The configuration at the chiral centers of the compounds of the formula I according to the invention is not known with certainty. Indications of the relative configuration at the various chiral centers emerge, though, from the "Nuclear Overhauser Effect" in proton nuclear resonance spectra and from the analysis of the alanine freed during hydrolysis. By analogy with the known absolute configuration, determined by X-ray structure analysis, of saframycin C (T. Arai et al., Tetrahedron Letters 1979, 2355) and of brominated safracin A (I. Ueda et al., Acta Cryst. C. 40, 1578 (1984), it is to be assumed that the compounds according to the invention have the spatial structure according to the formula

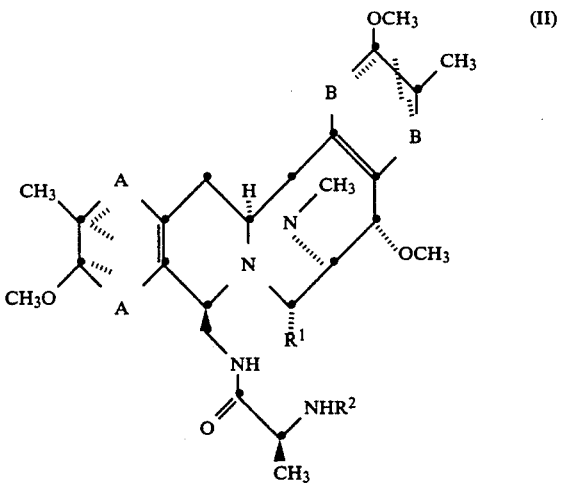

In compounds of formulae I and II, $R^2$ represents hydrogen or acyl. Acyl $R^2$ is especially the acyl group of a carboxylic acid or of a carbonic acid semiester having up to 20 carbon atoms, for example $C_1$–$C_{20}$-alkanoyl, $C_2$–$C_7$-alkanoyl substituted by hydroxy, by oxo or by halogen, aroyl or $C_1$–$C_7$-alkoxycarbonyl.

$C_1$–$C_{20}$-alkanoyl is preferably $C_1$–$C_7$-alkanoyl, for example formyl, acetyl, propionyl, n-butyryl, 2-methylpropionyl, n-pentanoyl, 2,2-dimethylpropionyl, 2-methylbutyryl, 3-methylbutyryl or n-hexanoyl, or straight-chained $C_8$–$C_{20}$-alkanoyl having an even number of carbon atoms, for example n-octanoyl, n-decanoyl, n-dodecanoyl, n-tetradecanoyl, n-hexadecanoyl, n-octadecanoyl or n-icosanoyl. $C_2$–$C_7$-alkanoyl substituted by hydroxy, by oxo or by halo is, for example, trifluoroacetyl, mono-, di- or tri-chloroacetyl, glycoloyl, glyceroyl, lactoyl, glyoxyloyl or pyruvoyl. Aroyl is, for example, benzoyl or 1- or 2-naphthoyl in which the phenyl or naphthyl ring may be substituted by nitro, amino, halogen, for example chlorine or bromine, hydroxy and/or by $C_1$-$C_4$-alkoxy, for example, methoxy, for example 4-nitrobenzoyl, 3,5-dinitrobenzoyl, anthraniloyl, 2,6-dichlorobenzoyl, salicyloyl, galloyl or 2-, 3- or 4-anisoyl. $C_1$-$C_7$-alkoxycarbonyl is, for example, methoxy-, ethoxy-, n-propoxy-, isopropoxy-, n-butoxy-, isobutoxy- or tert.-butoxy-carbonyl.

Preferred radical acyl $R^2$ is $C_1$-$C_7$-alkanoyl, especially acetyl.

Preferred are the compounds of formula I in which $R^1$ represents hydrogen or hydroxy, $R^2$ represents hydrogen, A represents C=O and B represents C=O or C—OH and the dashed line has the meaning given above, and pharmaceutically acceptable salts of such compounds. Also preferred are the compounds of formula I in which $R^1$ represents hydroxy, $R^2$ represents hydrogen, A represents C—OH and B represents C—OH and the dashed line has the meaning given above, and also the compounds of formula I in which $R^1$ represents hydroxy, $R^2$ represents acetyl, A represents C=O and B represents C=O and the dashed line has the meaning given above, and pharmaceutically acceptable salts of these compounds.

The invention relates especially to compounds of formula I in which $R^1$ represents hydrogen or hydroxy, $R^2$ represents hydrogen, A represents C=O and B represents C—OH and the dashed line has the meaning given above, and pharmaceutically acceptable salts of such compounds.

In the following, the compounds according to the invention are called saframycin Mx 1 ($R^1$=OH) and saframycin Mx 2 ($R^1$=H). Without any qualification these names indicate compounds of the formula I in which A is C=O and B is C—OH. With the qualification "BC" (bis-quinone) these names are used for compounds in which A represents C=O and B represents C=O. Saframycin Mx 1 BHC (bis-hydroquinone) is a compound of the formula I in which $R^1$ is OH, $R^2$ is hydrogen, A is C—OH and B is C—OH. The qualification "acyl" indicates corresponding compounds in which $R^2$ represents acyl.

Salts of compounds of the formula I according to the invention are especially pharmaceutically acceptable non-toxic acid addition salts. Examples of acid addition salts with non-toxic physiologically well tolerated acids are salts with inorganic acids, for example hydrochloric acid, sulphuric acid or phosphoric acid, or with organic carboxylic, sulphonic or sulpho acids, for example formic acid, acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also amino acids, for example α-amino acids, as well as methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid. For the purpose of isolation or purification it is also possible to use pharmaceutically unsuitable salts.

The compounds of the formula I according to the invention and their pharmaceutically acceptable salts have valuable pharmacological properties. For example, compounds of the formula I in which A represents C=O are effective in low concentrations of from 0.004 µg/ml to 0.3 µg/ml against various bacteria, for example against *Staphylococcus aureus, Bacillus subtilis, Micrococcus luteus* and *Escherichia coli*. In addition to antibiotic properties, the compounds also have tumour-inhibiting properties, for example against the experimental tumours leukaemia L 1210/S2, human pulmonary carcinoma MBA 9812, colon adenocarcinoma 26 and reticulosarcoma M5076.

If mice with leukemia L 1210/S2 are treated with i.p. injections of 2.5 or 5 mg/kg of saframycin Mx 2 on four successive days, then their lifespan is extended significantly by a factor of 1.6 or more. If treated with four injections of 0.625, 1.25 or 2.5 mg/kg of saframycin Mx 1 the lifespan is extended by a factor of 1.7 or more. Saframycin Mx 2 in 7 daily doses of 2.5 or 5.0 mg/kg i.p. significantly reduces the weight of human pulmonary carcinoma MBA 9812 experimentally implanted in balb/c nude mice to 62% or less compared with untreated animals. Saframycin Mx 1 in 10 doses of 1.25 mg/kg i.p. reduces the weight of colon adenocarcinoma 26 to 76% compared with untreated animals. After 17 doses of 1.25 mg/kg i.p. of saframycin Mx 1 the weight of reticulosarcoma M5076 is reduced even to 33% compared with untreated animals. The maximum tolerable single dose of saframycin Mx 1 and Mx 2 for mice is 12.5 mg/kg, and above 25 mg/kg, respectively.

The invention relates also to processes for the manufacture of compounds of formula I. Compounds of formula I are produced by growing the strain Mx x48 of the species *Myxococcus xanthus*, or a mutant derived therefrom, that produces compounds of formula I, in a culture containing carbon and nitrogen compounds and essential inorganic salts in an easily assimilable form at a temperature of from 15° C. to 40° C. and a pH value of from 5 to 9 under aerobic conditions, isolating the resulting compounds of formula I and, if desired, converting a resulting compound of formula I into a different compound of formula I and/or converting a resulting compound into a salt and/or converting a resulting salt into the free compound or into a different salt.

The invention relates also to the microorganism *Myxococcus xanthus*, strain Mx x48. It was isolated from a soil sample from Gabès Oasis, Tunisia, and deposited at the National Collection of Industrial and Marine Bacteria, Aberdeen, Scotland, under the number NCIB 12 268.

Strain Mx x48 is able spontaneously to form natural mutants that produce compounds of formula I. Artificial mutants can, for example, be produced chemically, for example by treatment with alkylating or nitrosating compounds, for example N-methyl-N'-nitro-N-nitrosoguanidine or with alkali nitrite, such as sodium nitrite, or by irradiation, for example with high-energy radiation, such as ultraviolet, X-ray or radioactive radiation. The invention relates also to such mutants of the strain Mx x48 that produce compounds of formula I.

In the process for the manufacture of compounds of formula I the microorganism *Myxocccus xanthus* strain Mx x48 is grown under suitable conditions.

The culture medium used for the growth must contain a carbon and nitrogen source and also essential inorganic salts. Suitable carbon and nitrogen sources are amino acids, peptides and proteins and also degradation products thereof, such as peptone or tryptone, and also meat extracts, powdered cereal, for example corn or wheat, beans, especially soya beans, fish meal, seeds, for example of cotton plants, distillation residues from the production of alcohol, yeast extracts etc. Essential inorganic salts contained in the nutrient solution may be, for example, chlorides, carbonates, sulphates, phosphates of alkali metals or alkaline earth metals, for example sodium, potassium, magnesium and calcium, and also salts of iron, zinc, manganese, molybdenum and copper. The growth is carried out preferably in liquid cultures, especially aqueous cultures.

A suitable liquid culture medium is especially MD1 (peptone from casein, tryptically digested, 0.3%; $CaCl_2.2H_2O$ 0.05%; $MgSO_4.7H_2O$ 0.2%). Other suitable liquid culture media consist, for example, of peptone from casein 0.05%, $CaCl_2.2H_2O$ 0.05%, $MgSO_4.7H_2O$ 0.02%, to which there may be added, as desired, 0.5% single cell protein, corn steep liquor, yeast extract, amino acid hydrolysate of casein, or protein from fish meal.

The culture is grown at temperatures of from 15° C. to 40° C., preferably at temperatures of from 25° C. to 35° C., for example at about 30° C. Suitable pH values are from 5 to 9, preferably from 6.5 to 8.5.

The growth can be carried out in stages, for example by a single or by several additions of nutrient solution, or can be carried out continuously by the continuous addition of nutrient solution. Preferably, the growth is in several stages, as follows: first a pre-culture is produced, for example in one of the mentioned culture media (inoculum), which is then, after about one to two days' fermentation, used to inoculate a larger culture, for example in a dilution ratio of from 1:10 to 1:500. This culture can in turn, after about two to three days' fermentation, be used to inoculate an even larger main culture, for example in a dilution ratio of from 1:10 to 1:100.

The first pre-culture can also be obtained by several days' growth of the strain Mx x48 on a solid or liquid culture medium, for example agar containing one of the mentioned liquid culture media. Suitable culture media are, for example, agar 1.5%, $CaCl_2.2H_2O$ 0.1%, containing baker's yeast 0.5% or peptone from casein 0.3% and yeast extract 0.1%.

The course of the fermentation can be followed analytically by sampling during fermentation, for example by measuring the pH value of the culture, which during fermentation rises from about pH 7.2 to about pH 8.0, by measuring the optical density which is a measure of the growth of the strain, gravimetrically by way of the dry weight of the biomass formed, by thin-layer chromatography, by reversed phase high-pressure liquid chromatography or by determining the antibiotic activity of the components contained in the culture filtrate. For example, cell-free culture supernatant in undiluted or diluted form can be tested in an agar diffusion test against *Staphylococcus aureus*.

The isolation of compounds of the formula I according to the invention from the culture liquor is carried out according to methods known per se taking into consideration their chemical, physical and biological properties. Thin-layer chromatography, for example on silica gel with methylene chloride/methanol, high-pressure liquid chromatography, for example on reversed phase silica gel, and/or the activity against *Staphylococcus aureus* in the agar diffusion test can be used to determine the concentration of the compounds according to the invention in the individual stages of isolation.

To isolate the compounds according to the invention from the crude fermentation liquor the latter is stirred, preferably for several hours, with macroporous non-ionic adsorber resins, for example synthetic resins having an aromatic basic structure, for example resins based on polystyrene, for example styrene/divinylbenzene copolymers. Such resins may be characterized by various customary statistical characteristics, for example pore volume, specific surface area, average pore diameter, most frequent pore diameter, distribution of pore sizes, distribution of particle sizes, and the like. Suitable adsorber resins have a pore volume of from about 0.5 to about 4.5 ml/g, a specific surface area of about 100–1000 $m^2$/g and an average pore diameter of from about 4 to about 130 nm, and are available, for example, under the trade names AMBERLITE®XAD-1, XAD-2 XAD-4, XAD-1180 and ER 180 of Rohm & Haas, DIAION®HP-10, HP-20, HP-21, HP-30, HP-40, HP-50 of Mitsubishi, DUOLITE®S-861, S-862, S-863 and ES 866 of Dia-Prosim, IMAC®Syn 46 and Syn 72 of Akzo Chemie, KASTEL®S-111, S-112, S-114 of Montedison, LEWATIT®OC.1031 of Bayer and RELITE® ADS of Resindion.

After separating the fermentation liquor from the adsorber resin, for example by sieving, the latter is washed with water and then eluted with an organic solvent or a mixture of water with an organic solvent that is inert towards the adsorber resin used, for example with isopropanol. The eluates are, if desired, treated with an organic or inorganic acid and concentrated in vacuo.

It is also possible to work up the fermentation mixture in a conventional manner. The culture liquor is for this purpose separated from the biomass in a customary manner, for example by filtration or centrifugation, and the culture filtrate is extracted with an organic solvent that is immiscible or only slightly miscible with water, for example methylene chloride, chloroform or, preferably, ethyl acetate. Concentration by evaporation in vacuo yields a crude extract. By partitioning the crude extract in a two-phase system consisting of two organic solvents immiscible with one another, for example methanol/heptane, the fermentation products, especially the compounds of formula I according to the invention, become enriched in the polar phase The crude extracts are purified preferably by chromatographic methods, for example by chromatography on an ion exchanger having weakly acidic functional groups, for example on an ion exchanger having carboxy groups, by adsorption or partition chromatography and/or high-pressure liquid chromatography on non-polar surfaces, for example on silica gel containing long-chained alkyl groups ("reversed phase") or on agarose with alkyl or phenyl groups ("hydrophobic interaction"). Other chromatographic methods are also suitable, for example affinity chromatography, "fast pressure liquid chromatography" and the like, and also countercurrent distribution, for example "droplet countercurrent chromatography" or "rotational locular countercurrent chromatography".

Suitable carriers for ion exchange chromatography are organic polymers, for example crosslinked agarose, dextran, polyacrylamide, styrene/divinylbenzene copolymer or cellulose. Preferably, this material carries weakly acidic functional groups, for example carboxy groups. Preferred ion exchangers are carriers of crosslinked dextran containing carboxyalkyl radicals, for example carboxymethyl radicals, such as are available, for example, under the trade name GM-Sephadex®.

An ion exchange material having carboxy groups is pretreated in a suitable aqueous buffer solution, for example a buffer solution of pH 5 to pH 7, for example phosphate buffer pH 5. Then, the crude extracts containing the compounds according to the invention are added, for example by applying these extracts to a column containing the pretreated ion exchanger. Substances and impurities that have not been bound are washed out of the ion exchanger column with buffer solution, if necessary under pressure, and the desired saframycins are eluted from the column by buffer solutions containing an increasing concentration of salt, for example phosphate buffer pH 5 containing increasing concentrations of sodium chloride. The described ion exchange chromatography can, if desired, also be carried out on columns suitable for high-pressure liquid chromatography.

Suitable carriers for adsorption and partition chromatography are, for example, organic polymers, for example crosslinked agarose, dextran or cellulose. Crosslinked dextrans that carry suitable functional groups, for example hydroxyalkyl groups, are preferred for the purification of the saframycins by adsorption and partition chromatography. Especially preferred is a crosslinked dextran having hydroxypropyl groups available under the trade name Sephadex ®LH-20.

Preferably, the extracts pre-purified by ion exchange chromatography are applied to a column containing a carrier having hydroxypropyl groups and eluted with mixtures of organic solvents of the same or a gradually changing composition. Preferably, methanol or mixtures of methanol with a further organic solvent of low polarity, for example methylene chloride, are used with the addition of an organic acid, for example formic or acetic acid, for example a methanol/methylene chloride mixture containing approximately 0.1% acetic acid. Like the ion exchange chromatography, it is also possible for the adsorption and partition chromatography to be carried out on columns suitable for high-pressure liquid chromatography.

To separate compounds of formula I, extracts prepurified by ion exchange chromatography and/or adsorption chromatography are subjected preferably to a high-pressure liquid chromatography on non-polar surfaces, so-called "reversed phase" chromatography. The carrier used for this is preferably one based on silica gel carrying long-chained alkyl groups, for example alkyl groups of 14 to 22 carbon atoms, for example 18 carbon atoms. Such carriers are available, for example under the trade names HD-Sil ®18-10-60, Nucleosil ®C-18, Bio-Sil ®ODS-10 or Hi-Pore ®RP-318. The saframycin mixture to be separated is applied to a reversed phase high-pressure liquid chromatography column and developed in aqueous organic solutions containing acid, for example in mixtures of water with methanol, acetonitrile or tetrahydrofuran containing an organic sulphonic acid, for example heptanesulphonic acid, trifluoroacetic acid or a weak inorganic acid, for example dihydrogen phosphate. Methanol/water mixtures with the addition of phosphate buffer pH 6.5 are preferred.

The purification of the crude extracts can also be carried out by countercurrent distribution chromatography, for example by "droplet countercurrent chromatography". Suitable aqueous phases are weakly acidic buffer solutions, for example buffer solutions of from pH 4 to pH 7, preferably phosphate buffer pH 5. The organic phase used is, for example, a chlorohydrocarbon, for example chloroform or methylene chloride, with which, if desired, a lower alkanol is mixed, for example n-butanol, iso- or n-propanol, or methanol, preferably a mixture of methylene chloride and isopropanol.

A compound of formula I is converted into a different compound of formula I by methods known per se, for example by oxidation, by reduction or by acylation.

The conversion of a hydroquinone (A and/or B represent C—OH) into the corresponding quinone (A and/or B represent C=O) by oxidation, and the conversion of a quinone into a hydroquinone by reduction, can be carried out, for example, analogously to the processes described in "Methoden der Organischen Chemie (Houben-Weyl)", 4th edition, volume VII/3a. Thieme Verlag Stuttgart 1977. Suitable mild oxidizing agents are, for example, metal salts and metal oxides, for example silver(I) oxide in diethyl ether, benzene or toluene in the presence of a drying agent, for example sodium sulphate, iron(III) salts, such as iron(III) chloride in water or aqueous ethanol, copper salts or thallium salts, for example thallium(III) trifluoroacetate. Another suitable oxidizing agent is atmospheric oxygen in neutral solution, for example in a buffer solution of pH 7 to pH 8. Suitable reducing agents are, for example, hydrogen in the presence of heterogeneous catalysts, for example platinum oxide or palladium-on-carbon, or homogeneous catalysts, for example tris(triphenylphosphine)rhodium(I) chloride, and also metal hydrides, for example borohydrides, such as sodium borohydride, or aluminium hydrides, such as lithium aluminium hydride, reducing salts, for example sodium dithionite, and also light in the presence of a hydrogen donor, for example normal daylight and methanol. The conversion of quinones and hydroquinones one into another can also be carried out by electrochemical methods, for example electrolysis in weakly acidic salt-containing solutions, for example buffer solutions of pH 4 to pH 6.

The acylation of a compound of the formula I in which $R^2$ represents hydrogen is carried out according to methods known per se, for example with an acid of the formula $R^2$—OH or with a reactive functional derivative of that acid.

If a free carboxylic acid is used for the acylation, the reaction is customarily carried out in the presence of a suitable condensing agent, for example a carbodiimide, for example dicyclohexyl- or preferably N-ethyl-N'-3-dimethylaminopropylcarbodiimide. The condensation is performed in an aqueous organic solvent mixture or an aqueous buffer close to neutral, for example from pH 6 to pH 8, optionally while cooling or heating and in an inert gas atmosphere, for example under nitrogen.

A reactive functional derivative of a carboxylic acid or of a carbonic acid semiester is a corresponding anhydride, for example a symmetric anhydride, for example acetic anhydride, a mixed anhydride of the acid $R^2$—OH with an inorganic or organic acid, for example with a hydrohalic acid, such as hydrochloric acid or hydrobromic acid, that is to say, for example, a carboxylic acid chloride or bromide or a chloroformic acid ester, or a mixed anhydride of a carboxylic acid with a semiester of carbonic acid, for example the ethyl or isobutyl semiester of carbonic acid. Another reactive functional derivative of a carboxylic acid or of a carbonic acid semiester is, for example, an activated ester, for example an N-hydroxyester, such as the ester with N-hydroxypiperidine, N-hydroxysuccinimide, N-hydroxyphthalimide or 1-hydroxybenztriazole.

The acylation reactions with reactive functional derivatives of $R^2$—OH are preferably carried out in aqueous organic homogeneous or two-phase solvent mixtures, if desired while cooling or gently heating, for example in a temperature range of from about 0° C. to about 40° C., preferably at about room temperature, and optionally in an inert gas atmosphere, for example under nitrogen. In this case an acid acceptor is added, for example a suitable organic base, for example an amine, for example trimethylamine, triethylamine, N-methylmorpholine, 1,5-diazabicyclo[4.3.0]non-5-ene, 1,8-diazabicyclo[5.4.0]undec-7-ene or pyridine, or an inorganic base, for example an alkali metal or alkaline earth metal hydroxide, for example sodium, potassium or calcium hydroxide, an alkali metal or alkaline earth metal carbonate, for example sodium carbonate, sodium hydrogen carbonate or calcium carbonate, or an alkali metal phosphate, for example sodium or potassium phosphate or hydrogen phosphate. Preferably, the acylation reaction is carried out in an aqueous buffer close to neutral, for example from pH 6 to pH 8, the buffer base assuming the role of acid acceptor. To inhibit the acylation of a phenolic hydroxy group A and/or B and, where applicable, of a hydroxy group $R^1$, for example an alcohol, for example methanol or ethanol, is added to the aqueous organic solvent mixture.

Salts of compounds of formula I can be manufactured in a manner known per se, for example by reacting the free compound with preferably stoichiometric amounts or a small excess of the acid forming an acid addition salt.

Salts can be converted into the free compounds in customary manner, for example by treatment with an equimolar amount of a free base, for example a hydroxide, such as an alkali hydroxide, for example lithium, potassium or sodium hydroxide, an alkaline earth hydroxide, for example calcium hydroxide or magnesium hydroxide, or an ammonium hydroxide, for example unsubstituted ammonium hydroxide or benzyltrimethylammonium hydroxide, or an organic tertiary amine, for example triethylamine. It should be noted, however, that the free compound of formula I is only of limited stability and, for storage, must be converted into an acid addition salt.

Salts of compounds of formula I are converted into other salts in a manner known per se. Preferably, the conversion of salts into other salts is carried out with ion exchangers that are charged with the desired anion, or by adsorption chromatography in a solvent that contains the acid of the desired acid addition salt in excess.

The invention relates also to those embodiments of the process in which an extract obtainable at any stage of the isolation is used as starting material and the concluding steps are carried out, the process is discontinued at any stage and/or a compound obtainable in accordance with the process according to the invention is further processed in situ.

The compounds of the present invention and the pharmaceutically acceptable salts thereof can be used, for example, for the manufacture of pharmaceutical preparations that contain an effective amount of the active ingredient preferably in admixture with a significant amount of inorganic or organic, solid or liquid, pharmaceutically acceptable carriers. The present invention relates also to pharmaceutical preparations, their manufacture and their use.

The pharmaceutical preparations according to the invention are suitable for oral or, preferably, parenteral, for example intravenous, intramuscular or topical, administration.

For example, the active ingredients of formula I of the present invention are used in the form of injectable, for example intravenously, intramuscularly, intradermally or subcutaneously administrable, preparations or infusion solutions. Such solutions are preferably isotonic aqueous solutions or suspensions which may be prepared before use, for example from lyophilised preparations that contain the active ingredient only or the active ingredient together with a carrier, for example dextran, mannitol or albumin. Pharmaceutical preparations for oral use are, if desired, sterilized and may contain adjuncts, for example preservatives, stabilisers, wetting agents and/or emulsifiers, solubilisers, salts for regulating the osmotic pressure and/or buffers. Also suitable are corresponding oily injection suspensions in which lipophilic solvents or vehicles, for example fatty oils, for example sesame oil, triglycerides or synthetic fatty acid esters, for example ethyl oleate, are used as carriers. The injectable pharmaceutical preparations which, if desired, may contain other pharmacologically valuable substances, for example other active ingredients, contain about from 0.1% to 100%, especially about from 1% to 50%, and in the case of lyophilisates up to 100%, of the active ingredient.

Suitable carriers for oral preparations, for example dragees, tablets or lacquer-coated tablets, are especially fillers, such as sugars, for example lactose, saccharose, mannitol or sorbitol, cellulose preparations and/or calcium phosphates, for example tricalcium phosphate or calcium hydrogen phosphate, binders, such as starch pastes based on, for example, corn, wheat, rice or potato starch, gelatin, methylcellulose, hydroxypropylmethylcellulose, hydroxypropylcellulose and/or polyvinylpyrrolidone, and/or, if desired, disintegrators, such as the mentioned starches, also carboxymethyl starch, crosslinked polyvinylpyrrolidone, agar, alginic acid or a salt thereof, such as sodium alginate, or low-molecular-weight carboxymethylcellulose. Adjuncts are especially flow-regulating agents and lubricants, for example silica, talc, stearic acid or salts thereof, such as magnesium or calcium stearate, and/or polyethyleneglycol.

Dragèe cores are provided with suitable coatings that may be resistant to gastric juices. Other orally administrable pharmaceutical preparations are dry-fill capsules made of gelatin and soft sealed capsules made of gelatin and a plasticizer, such as glycerin or sorbitol. Suitable rectally administrable pharmaceutical preparations are, for example, suppositories that consist of a combination of the active ingredient with a suppository base material. Orally and rectally administrable preparations contain from about 0.1% to about 50%, especially from about 1% to about 10%, of the active ingredient and, if desired, other pharmacologically valuable compounds.

Pharmaceutical preparations for topical uses are especially creams, gels, ointments, pastes, foams, tinctures and solutions that contain from about 0.05% to about 10%, especially from about 0.5% to about 5%, of the active ingredient.

The pharmaceutical preparations are manufactured in a manner known per se, for example by means of conventional dissolving, suspending, mixing or lyophilising processes described in pharmacopoeia.

The invention also relates to the use of the compounds of formula I or salts thereof as drugs, for example in the form of pharmaceutical preparations, for the treatment of bacterial infections by gram-positive bacteria and for the treatment of tumours, especially pulmonary and gastro-intestinal tumours and leukemia, in warm-blooded animals, for example humans and other mammals, by enteral, for example oral, or preferably parenteral, administration of therapeutically effective doses.

Depending on the species, age, individual condition, severity of the disease and method of administration, the daily doses are from about 0.01 mg to about 10 mg, especially from about 0.1 mg to about 1 mg, per kg of body weight, as considered appropriate by the doctor prescribing the treatment.

The following Examples illustrate the invention but do not limit the scope thereof in any way.

EXAMPLE 1

*Myxococcus xanthus* Mx x48 bacterium a) Origin and availability of the production strain The bacterium *Myxococcus xanthus* strain Mx x48 of the Myxococcaceae family of the order Myxobacterales was isolated in May 1980 from a soil sample from Gabès Oasis, Tunisia. The Mx x48 strain was deposited at the National Collection of Industrial and Marine Bacteria, Aberdeen, Scotland, on 26th May 1986 under the number NCIB 12 268 for patent purposes in accordance with the Budapest treaty.

b) Description of the production strain

Small vegetative rods, cylindrical with abruptly tapered ends, cigar-shaped, $0.8 \times 3.5$–5 μm, move on surfaces in a crawling-gliding manner. On suitable media, for example VY/2-agar (see below), the organism forms "fruiting bodies" 50–150 μm in diameter in the form of intensely red-orange to blue-grey soft-slimy drops, vesicles or capituli on the agar surface. Inside them are spherical, strongly refracting myxospores 1.8–1.9 μm in diameter. The colonies tend to spread like wafts as "swarms" on the agar surface and can become up to several centimeters in size. On some media they are intensely greenish-yellow to orange in color.

c) Culture conditions

The organism grows well on peptone agar, for example CY-agar (Casitone [Difco] 0.3%, yeast extract [Difco] 0.1%, $CaCl_2.2H_2O$ 0.1%, agar 1.5%, pH 7.2) or on yeast agar, for example VY/2 agar (baker's yeast 0.5% based on fresh weight, $CaCl_2.2H_2O$ 0.1%, agar 1.5%, pH 7.2). In liquid media Mx x48 grows in homogeneous cell suspension both in shaken flasks (at approximately 160 revs/min) and in bioreactors. A suitable culture medium is, for example, MD1 l.m. (peptone from casein, tryptically digested [Merck, Darmstadt] 0.3%, $MgSO_4.7H_2O$ 0.2%, $CaCl_2.2H_2O$ 0.05%, pH 7.2). Mx x48 is strictly aerobic. All cultures are maintained at 30° C. The generation time in MD1 l.m. is approximately 6.5 hours ($\mu = 0.15$ per hour). The maximum achieved optical density (623 nm, 1 cm path length) is from 1.3 to 1.5. The concentration of the peptone from casein can also be increased, for example to 0.5 or 1%. The generation time does not vary in this case, but the optical density, by contrast, increases to approximately 2 or 3.5 respectively. As the concentration of peptone increases, however, the production of antibiotic becomes lower compared with the production in MD1 l.m. Suitable culture media in which the strain grows with antibiotic formation are also the following: 0.05% casitone, 0.2% $MgSO_4.7H_2O$ and 0.05% $CaCl_2.2H_2O$, pH 7.2, containing either 0.5% Probion S (single cell protein, Hoechst) or 0.5% corn steep liquor or 0.5% Protaminal (fish protein concentrate, Asta) or 0.5% yeast extract or 0.3% casamino acids (Difco)

d) Possible preservation methods

1. By freezing vegetative cells of plate or liquid cultures in peptone solution at −80° C. (viable for several years). 2. By drying fruiting bodies on filter paper (viable for several years at room temperature). 3. By drying fruiting bodies in milk, and storing under nitrogen at room temperature in ampoules sealed by melting (viable for several years). 4. By suspending vegetative cells of plates or liquid cultures in peptone solution and freezing in liquid nitrogen (viable for several years).

EXAMPLE 2

Manufacture of cell supernatants with antibiotic activity a) Conditions of production It is possible to detect the activity against *Staph. aureus* at the end of the logarithmic growth phase (OD 0.9–1) using the agar diffusion test in shaken flasks. The highest activity is achieved in the early stationary phase. The pH in the culture at that time is about 8 and on further incubation rises to about 8.5 without the optical density increasing further. In the late stationary phase instead the cells become clumped and cell lysis occurs. The antibiotic activity in this case falls again.

b) Production in a fermenter

1. Preculture: 50 ml of MD1 l.m. are inoculated with 0.5 ml and maintained at 30° C. and 160 revs/min for 2 days.

2. Prefermentation: a 25 liter bioreactor marketed by Braun, Melsungen, having a blade agitator system is filled with MD1 l.m. medium and inoculated with the preculture (No. 1). The temperature is maintained at 30° C. The speed of rotation of the agitator is 200 revs/min and the aeration 0.1 $Nm^3/h$. Without further modifications the fermentation is carried out over a period of 66 hours. After this time an OD (623 nm) of 1.1 and a pH of 7.9 are achieved.

3. Main fermentation: A bioreactor with a capacity of 700 liters, marketed by Giovanola, Monthey, Switzerland and having a blade agitator system is filled with MD1 l.m. medium. After inoculation with the prefermentation product (No. 2) a speed of rotation of 150 revs/min and an aeration of 1 $Nm^3/h$ are set. By increasing the aeration and the speed of revolution the oxygen partial pressure is maintained above 60% saturation during the course of the cultivation. After 50 hours an OD of 1.3 and a pH of 8 are achieved. The culture supernatant now contains the antibiotic. In the agar diffusion test against *Staph. aureus*, a just about still visible inhibiting areola (approximately 7 mm in diameter) is obtained when the culture supernatant is diluted 1:64.

EXAMPLE 3

Isolation and purification of the saframycins a) Working up a 700 liter fermentation When the fermentation of Example 2b) is complete, 4.0 liters of XAD-resin ER-180 ® (marketed by Rohm & Haas) are introduced into the culture liquor. The mixture is stirred slowly for 5 hours. The resin is separated from the cells in which there is no antibiotic and from the medium using a seive. It is transferred into a chromatography column and eluted in one pass with 12 liters (1 liter/hour) of isopropanol. Over 90% of the antibiotic complex is eluted with the first 6 liters of isopropanol. Immediately 0.1% (v/v) acetic acid is added to the fractions containing saframycins and the whole is concentrated in a rotary evaporator in brown flasks. The concentrated XAD extract weighs 27 g.

Saframycins Mx 1 and Mx 2 are basic, light-sensitive and oxidation-sensitive hydroquinone/quinone derivatives that are stable only at pH values of less than 7. Purification is therefore carried out substantially with the exclusion of light and at pH values around 5. Temporary storage of the substance-containing fractions is in brown-tinted glass containers, and long-term storage is at $-70°$ C.

b) Purification of the saframycins

The crude extract is dissolved in 300 ml of 0.07M phosphate buffer pH 5 and applied to an open column filled with 1 liter of swelled CM-Sephadex ®C-25 marketed by Pharmacia in 0.07M phosphate buffer pH 5. First of all, any material that has not been absorbed is eluted with 2 liters of phosphate buffer. In a further step weakly adsorbed material is washed down with 1 liter of 0.07M phosphate buffer pH 5/0.2M sodium chloride. The antibiotic complex is eluted from the column completely using 2 liters of 0.07M phosphate buffer pH 5/0.5M NaCl, which is visible by a migrating yellowish band. After concentration of the eluate and repeated extraction of the residue with ethanol, approximately 2.5 g of highly active material are obtained. This still contains residues of the phosphate salt. To remove the salt chromatography is carried out on a Sephadex ®LH-20 column with methanol and 1% formic acid or acetic acid as eluant, phosphate being exchanged for formate or acetate, respectively. Basic impurities still contained in the eluate, such as 2-phenylethylamine and 2-(4-hydroxyphenyl)-ethylamine are eliminated by chromatography on Sephadex ®LH-20 with dichloromethane/methanol 1:1/1% formic acid or acetic acid. 700 mg of a product are obtained which, according to analytical HPLC (Nucleosil ®C-18, 7.5 μm, methanol/water 60:40/0.005M heptanesulphonic acid) contains as the main products the two saframycins Mx 1 and Mx 2, and also the bis-quinone derivatives saframycin Mx 1 BC and Mx 2 BC and the bis-hydroquinone derivative Mx 1 BHC.

c) Separation of the saframycins

The mixture of saframycins is separated by semi-preparative HPLC on HD-Sil ®18-10-60 (marketed by Organogen, 25 cm×16 mm) with methanol/water 1:1/0.5% triethylammonium formate buffer pH 6.0. At a flow of 25 ml/min, Mx 1 is eluted after 6.4 minutes and Mx 2 after 9.2 minutes. Both substances are obtained in the form of viscous red-brown oils. The secondary component Mx 1 BHC is eluted before Mx 1, and the secondary components Mx 1 BC and Mx 2 BC are eluted in that order after Mx 2.

Example 4
Characterisation of the saframycins

(a) Saframycin Mx 1 and Mx 2

| | Saframycin Mx 1 ($R^1$ = OH) | Saframycin Mx 2 ($R^1$ = H) |
|---|---|---|
| Thin-layer elution behaviour ($R_f$ values) | | |
| Silica gel 60 F 254 ethyl acetate | 0 | 0 |
| $CH_2Cl_2/CH_3OH$ 9:1 | 0.23 | 0.20 |
| $CH_3OH$ | 0.47 | 0.36 |
| RP-18 Nano-Sil $C_{18}$-100 $CH_3OH/H_2O$ 4:1 | 0.67 | 0.65 |
| Colour reaction TLC identical for both saframycins. Ninhydrin: red-violet, Dragendorff: red-brown, hydroxylamine/iron (III) chloride: intense yellow, 254 nm: fluorescence extinction. | | |
| HPLC-retention time on HD-Sil 18-10-60 $CH_3OH/H_2O$ 3:2/0.005 M $C_7H_{15}SO_3H$ | 4.97 min. | 6.38 min. |
| UV-spectrum $\lambda_{max}$ (log ε), c = 2 in $CH_3OH$ | 273 nm (3.95) | 273 nm (3.97) |
| Optical rotation $[\alpha]_D^{25}$ | $-70.7°$ | $-119.8°$ |
| IR-spectrum as a film, $\nu$ ($cm^{-1}$) (sh = shoulder) | 3200, 2900, 1657, 1619(sh), 1459, 1300, 1236, 1158. | 3200, 2900 1680(sh), 1656, 1623(sh), 1461, 1236, 1159, 1122. |
| FAB-MS | | |
| Negative ions range | m/e 568 (M—OH)—H | — |
| Positive ions range | — | m/e 569 M—H$^+$ |
| Elemental analysis | monophosphate.$H_2O$ | monoformate.$H_2O$ |
| Emperical formula: | $C_{29}H_{43}N_4O_{14}P$ (702.7) | $C_{30}H_{42}N_4O_{11}$ (640.67) |
| Calculated: | C 49.56 H 6.17 N 7.97% | C 56.20 H 6.60 N 8.70% |
| Found: | C 50.17 H 6.33 N 7.66% | C 56.36 H 6.70 N 8.94% |

NMR-Spectrum: 15 mg of monophosphate in 0.5 ml $CD_3OD$
s = singlet, d = doublet, t = triplet, q = quartet, m = multiplet, dd = double doublet, ddd = triple doublet

| | Saframycin Mx 1 | | Saframycin Mx 2 | |
|---|---|---|---|---|
| $^1$H—NMR Proton | (ppm) | Couling constants (Hz) | (ppm) | coupling constants (Hz) |
| 1-H | 4.33 s | (1–4b) 3.0; (1–22a) 0.5; (1–22b) 2.5; | 3.59 m | (1–4a) 1.5; (1–4b) 3.5; (1–22a) 3.6; (1–22b) 1.5; |
| 3-H | 3.50 ddd | (3–4a) 2.5; (3.14 4b) 11; (3–11) 1.0; | 3.12 ddd | (3–4a) 3; (3–4b) 11; (3–11) 3; |
| 4-H$_a$ | 3.12 dd | (4a–4b) 17.5; | 3.04 ddd | (4a–4b) 18; |
| 4-H$_b$ | 1.51 ddd | | 1.59 ddd | |
| 11-H | 4.75 dd | (11–13) 1.0; | 4.90 dd | (11–13) 1.5; |
| 12-CH$_3$ | 2.84 s | | 2.88 s | |
| 13-H | 4.20 s | (13–14) 2.8; (13–21) below 0.5; | 4.13 d | |

Example 4
Characterisation of the saframycins -continued

| | Saframycin Mx 1 | | Saframycin Mx 2 | |
|---|---|---|---|---|
| 14-H | 4.82 d | | 4.95 s | |
| 21-H$_a$ | 4.78 s | | 3.11 dd | (21a–21b) 13; (21a–13) 3; |
| 21-H$_b$ | — | | 3.71 d | |
| 22-H$_a$ | 3.77 dd | (22a–22b) 14.0; | 4.09 dd | (22a–22b) 14.5; |
| 22-H$_b$ | 3.25 dd | | 3.34 dd | |
| 24-H | 3.69 q | (24–25) 7.0; | 3.68 q | (24–25) 7.1; |
| 25-H$_3$ | 0.93 d | | 0.82 d | |
| 7-OCH$_3$ | 4.02 s | 4.02 s | | |
| 17-OCH$_3$ | 3.75 s | | 3.75 s | |
| 14-OCH$_3$ | 3.72 s | | 3.69 s | |
| 16-CH$_3$ | 2.25 s | | 2.26 s | |
| 6-CH$_3$ | 1.93 s | | 1.93 s | |

| $^{13}$C—NMR C-Atom | Saframycin Mx 1 (ppm) | Saframycin Mx 2 (ppm) |
|---|---|---|
| 1 | 54.63 d | 61.11 d |
| 3 | 51.80 d | 57.07 d |
| 4 | 25.60 t | 26.19 t |
| 5 | 186.95 s | 187.17 s |
| 6 | 129.33 s | 128.87 s |
| 7 | 157.23 s | 157.37 s |
| 8 | 182.77 s | 182.91 s |
| 9 | 143.10 s | 143.04 s |
| 10 | 138.43 s | 137.63 s |
| 11 | 58.19 d | 58.15 d |
| 12-CH$_3$ | 42.15 q | 41.39 q |
| 13 | 59.98 d | 59.38 d |
| 14 | 72.98 d | 75.39 d |
| 15 | 147.16 s | 146.58 s |
| 16 | 123.44 s | 123.36 s |
| 17 | 148.07 s | 147.75 s |
| 18 | 142.74 s | 143.04 s |
| 19 | 112.20 s | 113.04 s |
| 20 | 119.36 s | 120.75 s |
| 21 | 89.23 d | 54.44 t |
| 22 | 41.39 t | 39.36 t |
| 23 | 170.85 s | 170.65 s |
| 24 | 50.02 d | 49.85 d |
| 25 | 17.16 q | 17.08 q |
| 6-CH$_3$ | 8.76 q | 8.81 q |
| 16-CH$_3$ | 9.87 q | 9.98 q |
| 7-OCH$_3$ | 61.45 q | 61.04 q |
| 17-OCH$_3$ | 61.02 | 61.44 q |
| 14-OCH$_3$ | 58.19 q | 58.07 q |

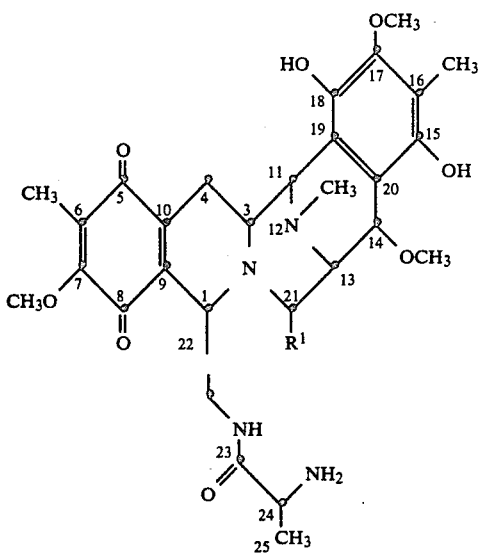

(b) Saframycins Mx 1 BC, Mx 2 BC and Mx 1 BHC

| | Saframycin Mx 1 BC | Saframycin Mx 2 BC | Saframycin Mx 1 BHC |
|---|---|---|---|
| Thin-layer elution behaviour (R$_f$-values) | | | |
| Silica gel 60 F 254 ethyl acetate | 0 | 0 | |
| CH$_2$Cl$_2$/CH$_3$OH 9:1 | 0.52 | 0.53 | |
| CH$_3$OH | 0.54 | 0.51 | |
| RP-18 Nano-Sil C$_{18}$-100 CH$_3$OH/H$_2$O 4:1 | 0.61 | 0.56 | |

-continued

Example 4
Characterisation of the saframycins

| | | | |
|---|---|---|---|
| HPLC-retention time on HD-Sil 18-10-60 CH$_3$OH/H$_2$O 3:2/0.005 M C$_7$H$_{15}$SO$_3$H | 7.55 min | 10.86 min | 3.5 min |
| UV-spectrum $\lambda_{max}$ (log $\epsilon$) | 264 nm (4.32) | 264 nm (4.32) | 291 nm |
| $^1$H—NMR spectrum $\delta$ (ppm) in CD$_3$OD | 4.05 and 4.04 (each s,3H, 7-OCH$_3$ and 17-OCH$_3$) | 4.05 and 4.02 (each s,3H, 7-OCH$_3$ and 17-OCH$_3$) | 3.78 (s,3H, 17-OCH$_3$) 3.70 (s,6H, 7-OCH$_3$ and 14-OCH$_3$) |
| | 3.59 (s,3H, 14-OCH$_3$) | 3.59 (s,3H, 14-OCH$_3$) | |
| | 2.47 (s,3H, 12-CH$_3$) | 2.46 (s,3H, 12-CH$_3$) | 2.95 (s,3H, 12-CH$_3$) |
| | 2.00 (s,3H, 16-CH$_3$) | 2.00 (s, 3H, 16-CH$_3$) | 2.27 (s,3H, 16-CH$_3$) |
| | 1.94 (s,3H, 6-CH$_3$) | 1.94 (s,3H, 6-CH$_3$) | 2.17 (s,3H, 6-CH$_3$) |
| | 1.28 (d,3H, 25-H$_3$) | 1.29 (d,3H, 25-H$_3$) | 1.22 (d,3H, 25-H$_3$) |

EXAMPLE 5

Conversion of saframycins a) Oxidation of saframycin Mx 1 to Mx 1 BC with atmospheric oxygen 10 mg of saframycin Mx 1 (in the form of the monophosphate) are dissolved in 2 ml of phosphate buffer pH 7.3 and the whole is stirred for 20 minutes in an open flask. The pH value is adjusted to about 6 with dilute phosphoric acid and the solution is concentrated under an oil pump vacuum. The residue is repeatedly taken up in isopropanol, the buffer salts remaining. The isopropanol solution contains 9.5 mg of saframycin Mx 1 BC.

Saframycin Mx 2 is oxidized to saframycin Mx 2 BC in an analogous manner.

b) Reduction of saframycin Mx 1 to Mx 1 BHC with hydrogen

In a hydrogenation vessel, 10 mg of saframycin Mx 1 (in the form of the monophosphate) are dissolved in 0.5 ml of methanol and 0.5 ml of water, a spatula tip of palladium-on-activated carbon (10% Pd) is added and the whole is shaken for 10 minutes in a weak stream of hydrogen. The catalyst is subsequently filtered off under a nitrogen atmosphere and the solution, which contains 10 mg of Mx 1 BHC, is concentrated.

Saframycin Mx 1 BHC is unstable and is re-oxidized regiospecifically to saframycin Mx 1 quinone/hydroquinone) in the presence of atmospheric oxygen.

c) Acetylation of saframycin Mx 1

15 mg of saframycin Mx 1 are dissolved in 2 ml of methanol and 2 ml of phosphate buffer pH 7.3, 0.05 ml of acetic anhydride is added and the whole is stirred overnight at room temperature. The reaction solution is concentrated, taken up in a small amount of water and applied to an XAD-2 column. Salts are washed out with 2 bed volumes of water. The product is then eluted with 1 bed volume of methanol. The methanol solution containing 15 mg of acetyl-saframycin Mx 1 BC is concentrated in vacuo.

UV-spectrum in methanol: $\lambda_{max}$ 266 nm, log $\epsilon$ 4.32
FAB-MS in positive ions range:
 expected: m/e 627 (M+H)+
 found: m/e 613 (100%), [M+2xH−1x0]+H+
 m/e 615 (30%), [M+4xH−1x0]+H+ High resolution for C$_{31}$H$_{41}$N$_4$O$_9$ cal. 613.2873, found 63.2859.

$^1$H-NMR in CD$_3$OD: 4.05 and 4.02 (each s,3H, 7-OCH$_3$ and 17-OCH$_3$), 3.55 (s,3H, 14-OCH$_3$), 2.43 (s,3H, 12-CH$_3$), 2.00 (s,3H, 16-CH$_3$), 1.95 (s,3H, 6-CH$_3$), 1.75 (s,3H, acetyl-CH$_3$), 1.0 (d,3H, 25-H$_3$)

EXAMPLE 6

Determination of the minimum inhibiting concentration of saframycins Mx 1 and Mx 2

The test organisms, in a cell density of 10$^5$ cells/ml (*Myxococcus xanthus*: 10$^7$ cells/ml) each, are placed in the appropriate nutrient media in test tubes.

The media used are, for *Myxococcus xanthus*: MD1 l.m.; for other bacteria: peptone from casein, tryptically digested (Merck) 0.5%, proteose-peptone (Difco) 0.5%, meat extract (Oxoid) 0.1% pH 7.0; for yeasts: bactopeptone (Difco) 1%, yeast extract (Difco) 1%, glycerin 2%, pH 6.3.

A series of concentrations of the saframycins Mx 1 and Mx 2 dissolved in methanol are added to the cell suspensions of the test organisms and the test tubes are incubated for 18 to 40 hours at 30° C.

The minimum inhibiting concentrations of saframycins Mx 1 and Mx 2 are listed in the following Table:

TABLE

| Test organism | Saframycin Mx 1 ($\mu$g/ml) | Saframycin Mx 1 ($\mu$g/ml) |
|---|---|---|
| *Staphylococcus aureus* GBF 16 | 0.004 | 0.5 |
| *Bacillus subtilis* DSM 10 | 0.063 | 1 |
| *Micrococcus luteus* DSM 348 | 0.001 | 0.063 |
| *Escherichia coli* CG 164 | 0.08 | 5 |
| *Escherichia coli* tol C | 0.32 | 20 |
| *Proteus morganii* CG 166 | 1.25 | >20 |
| *Myxococcus xanthus* Mx x48 | 20 | not tested |
| *Saccharomyces cerevisiae* GBF 26 | >20 | >20 |

Towards *Staph. aureus* the bis-quinones Mx 1 BC and Mx 2 BC have similar activities to Mx 1 and Mx 2. The bis-hydroquinone Mx 1 BHC is not stable under the test conditions.

EXAMPLE 7

Pharmaceutical preparation for parenteral administration 5 ml portions of a sterile aqueous solution of 1% saframycin Mx 1 (in the form of the phosphate monohydrate) are each introduced under aseptic conditions into 5 ml ampoules or vials and freeze-dried. The ampoules or vials are sealed under nitrogen and checked.

Solutions of saframycin Mx 2, Mx 1 BC, Mx 2 BC, Mx 1 BHC and acetyl-Mx 1 BC are processed in the same manner.

We claim:

1. A biologically pure culture of the strain Mx x48 of the microorganism *Myxococcus xanthus*, deposited at the National Collection of Industrial and Marine Bacteria, Aberdeen, Scotland, under the number NCIB 12 268, or a mutant derived from that strain, which produces a compound of the formula I in a recoverable amount:

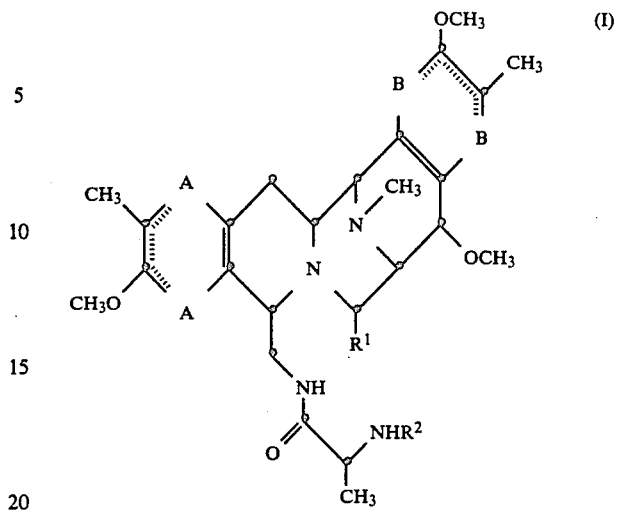

in which R[1] represents hydrogen or hydroxy, R[2] represents hydrogen and A and B, independently of one another, each represents C=O or C—OH, and wherein the dashed line represents a C=C double bond at the position of the middle bond when A or B represents C=O, or at the position of the two outer bonds when A or B represents C—OH, and salts of such compounds.

* * * * *